(12) United States Patent
Ferry

(10) Patent No.: US 8,911,400 B2
(45) Date of Patent: Dec. 16, 2014

(54) SYSTEM FOR INTRALUMINAL TRAVEL WITHIN LIVING VASCULATURE

(75) Inventor: Steven J. Ferry, Excelsior, MN (US)

(73) Assignee: Steve Ferry, Excelsior, MN (US)

(*) Notice: Subject to any disclaimer, the term of this patent is extended or adjusted under 35 U.S.C. 154(b) by 42 days.

(21) Appl. No.: 12/028,394

(22) Filed: Feb. 8, 2008

(65) Prior Publication Data

US 2008/0200874 A1 Aug. 21, 2008

Related U.S. Application Data

(60) Provisional application No. 60/889,145, filed on Feb. 9, 2007.

(51) Int. Cl.
  *A61M 31/00* (2006.01)
  *A61M 37/00* (2006.01)
  *A61M 25/00* (2006.01)
  *A61M 25/01* (2006.01)

(52) U.S. Cl.
  CPC ....... *A61M 25/0108* (2013.01); *A61M 25/0045* (2013.01)
  USPC .......... 604/103.1; 604/524; 604/527

(58) Field of Classification Search
  CPC ............. A61M 25/0053; A61M 25/0054; A61M 25/005; A61M 25/0108; A61M 2025/0042; A61M 25/0012; A61M 25/0045; A61M 2025/1079; A61M 25/0041; A61M 25/10; A61M 25/0009; A61M 25/0043; A61M 2025/0046; A61M 2025/006; A61B 17/3421; A61B 17/12022; A61B 17/12136
  USPC ....................................... 604/103.1
  See application file for complete search history.

(56) References Cited

U.S. PATENT DOCUMENTS

| | | | |
|---|---|---|---|
| 6,306,124 B1 * | 10/2001 | Jones et al. .............. | 604/509 |
| 6,858,024 B1 | 2/2005 | Berg et al. | |
| 6,939,337 B2 * | 9/2005 | Parker et al. .............. | 604/528 |
| 7,207,980 B2 * | 4/2007 | Christian et al. ........... | 604/524 |
| 2002/0032408 A1 | 3/2002 | Parker et al. | |
| 2002/0035331 A1 | 3/2002 | Brockway et al. | |
| 2002/0156459 A1 * | 10/2002 | Ye et al. .................. | 604/527 |
| 2003/0167031 A1 * | 9/2003 | Odland .................... | 604/8 |
| 2005/0004556 A1 | 1/2005 | Pursley | |

(Continued)

FOREIGN PATENT DOCUMENTS

| | | |
|---|---|---|
| KR | 1020020026598 | 4/2002 |
| KR | 20030020923 A | 3/2003 |

(Continued)

OTHER PUBLICATIONS

International Application Serial No. PCT/US2008/053433, Search Report mailed Jul. 28, 2008, 3 pgs.

(Continued)

*Primary Examiner* — Jason Flick
(74) *Attorney, Agent, or Firm* — Schwegman Lundberg & Woessner, P.A.

(57) ABSTRACT

Embodiments of the invention include a catheter, comprising: a lumen having a distal end and a proximal end; one or more marker bands circumferentially arranged around the lumen; a support structure extending from the proximal end of the lumen to the most distal marker band; and a top jacket positioned annularly with respect to the lumen, comprising five durometers of material, wherein the support structure and top jacket alternate along the length of the catheter.

8 Claims, 3 Drawing Sheets

(56) References Cited

U.S. PATENT DOCUMENTS

| | | |
|---|---|---|
| 2006/0074401 A1 | 4/2006 | Ross |
| 2006/0210605 A1* | 9/2006 | Chang et al. .............. 424/434 |
| 2009/0036768 A1* | 2/2009 | Seehusen et al. .......... 600/424 |
| 2011/0245802 A1* | 10/2011 | Hayman et al. ............ 604/509 |

FOREIGN PATENT DOCUMENTS

| | | |
|---|---|---|
| KR | 1020030020923 | 3/2003 |
| WO | WO-03/020353 A1 | 3/2003 |
| WO | WO-03020353 A1 | 3/2003 |
| WO | WO-2007013545 A1 | 2/2007 |
| WO | WO 2007013545 A1 * | 2/2007 |
| WO | WO-2008098176 A2 | 8/2008 |
| WO | WO-2008098176 A3 | 8/2008 |

OTHER PUBLICATIONS

International Application Serial No. PCT/US2008/053433, Written Opinion mailed Jul. 28, 2008, 7 pgs.

"European Application Serial No. 08729401.3, Response filed Dec. 30, 2011 to European Search Report rnailed Jun. 16, 2011", 10 pgs.

"Chinese Application Serial No. 200880008059.8, Office Action Received Jul. 5, 2011", (w/ English Translation), 12 pgs.

"Chinese Application Serial No. 200880008059.8, Response filed Nov. 21, 2011 to Office Action mailed Jul. 5, 2011", 4 pgs.

"European Application Serial No. 08729401.3,Extended European Search Report mailed Jun. 16, 2011", 6 pgs.

\* cited by examiner

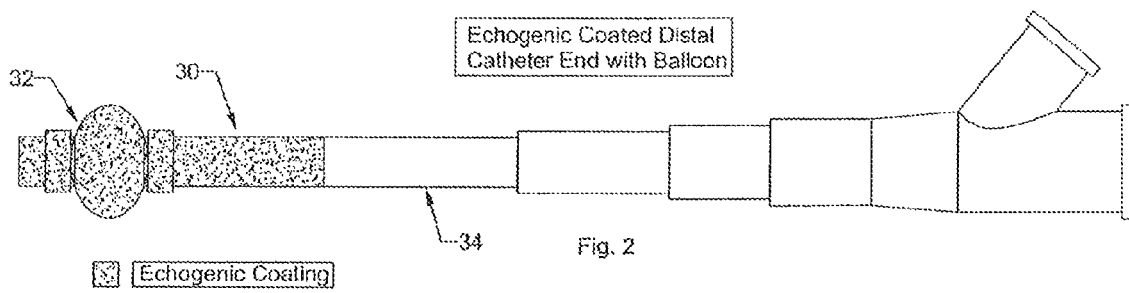
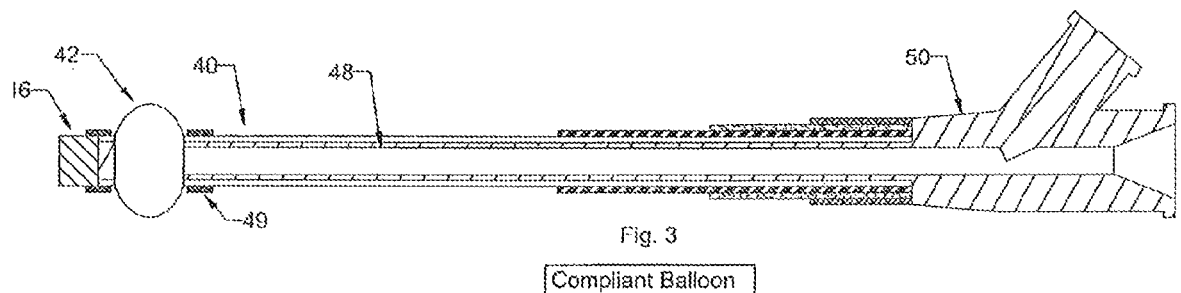
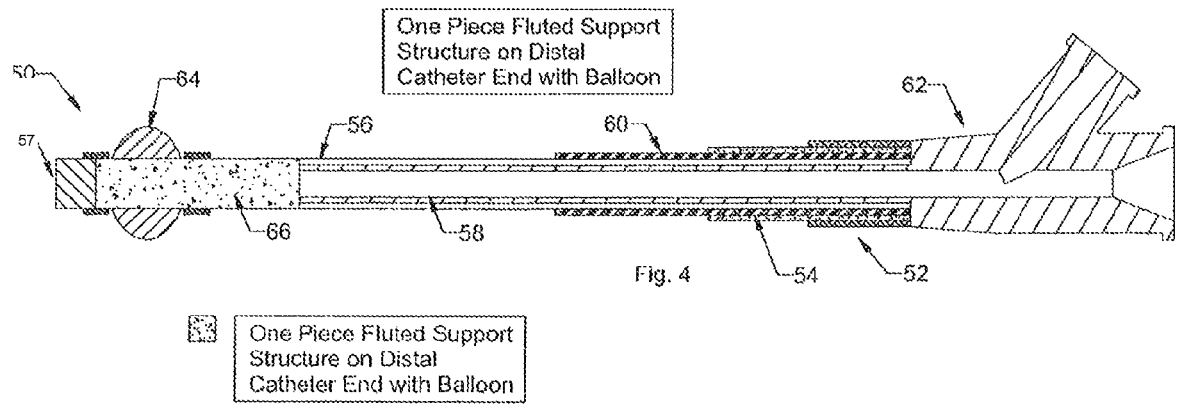

SYSTEM FOR INTRALUMINAL TRAVEL WITHIN LIVING VASCULATURE

CROSS REFERENCE TO RELATED APPLICATIONS

This application claims the benefit of priority of U.S. Provisional Application Ser. No. 60/889,145, filed Feb. 9, 2007 which is incorporated herein by reference in its entirety.

FIELD

Inventive subject matter described herein relates to a flexible catheter system for navigating through tortuous paths within the vasculature of living beings and to method embodiments for making the flexible catheter system and to embodiments for using the flexible catheter system.

LIMITED COPYRIGHT WAIVER

A portion of the disclosure of this patent document contains material to which the claim of copyright protection is made. The copyright owner has no objection to the facsimile reproduction by any person of the patent document or the patent disclosure, as it appears in the U.S. Patent and Trademark Office file or records, but reserves all other rights whatsoever. Copyright 2007, Steven Ferry.

BACKGROUND

Since the 1980's, microcatheter technology has advanced to become commonplace in the treatment of vascular lesions of the central nervous system and other systems having tiny, tortuous vasculature. Microcatheters have been used to treat cerebral aneurysms, fistulas, and arterial venous malformations, for example, by occluding the parent vessel. Microcatheters have been used as well to deliver agents to open occluded vasculature, including agents to dissolve clots. Balloon microcatheters have been used to open vessels narrowed due to atherosclerosis.

Microcatheters have also been used to treat pathological vascular abnormalities through an endovascular approach, using selective deposition of coils, particles, or liquid adhesives. Microcatheters have additionally been used to deliver chemotherapeutic agents to spinal, head and neck, or intracranial malignancies.

Conventionally, for some embodiments, microcatheters have advanced from a femoral puncture through the lumen of a guiding catheter which has terminated in a carotid or vertebral artery. The microcatheter is advanced beyond the guiding catheter using one of two known techniques. One prior art technique has been directing a guide wire through the lumen of the microcatheter which has had varying degrees of tipshape, torqueability, stiffness and external coating. A second prior art method has included a flow-directed technique in which the microcatheter has been extremely flexible and has been carried by blood flow to the lesion, assisted by of injections of saline or contrast media through the flow directed microcatheter.

Each of the conventional methodologies for delivering a microcatheter has had drawbacks. The guidewire directed microcatheter has involved the risk of puncturing a vessel or aneurysm, which has had the potential of having devastating hemorrhagic consequences intracranially. With the flow-directed microcatheter, it has frequently been difficult to make precise turns and select individual vessels when complex vascular anatomy has been encountered.

A guidewire has not been usable in the flow-directed microcatheter because of the suppleness of the microcatheter and the significant possibilities of puncturing the wall of the microcatheter with a stiff guidewire. This risk has also prohibited the delivery of coils which have been used to assist in occlusion, through a flow-directed microcatheter. Thus, only liquid adhesive or tiny particles have been injected through the flow-directed variety of microcatheter for vascular occlusion, the tiny particles usually of insufficient size to achieve the desired vascular occlusion. Conversely, the guide-wire directed microcatheter often times has not been pushable from the groin over a guidewire through multiple turns in branching intracranial vascularity to reach the desired vessel.

In one prior art attempt at improvement of these techniques, a method has been developed to incorporate a balloon into the tip of a microcatheter to allow the blood flow to carry the distended balloon distally to the desired target vessel. The disadvantage with the balloon technology is that two lumens have been required, one for the lumen to deliver the embolic agent, and the second balloon to inflate and deflate the balloon. Alternatively, a calibrated leak balloon has been incorporated in the tip of the microcatheter. This, however, has not allowed for directionality and has not been usable with a guidewire.

DESCRIPTION OF THE DRAWINGS

FIG. 2 illustrates a cross-sectional view of one embodiment of the catheter system that includes an echogenic coated distal end.

FIG. 3 illustrates a cross-sectional view of one embodiment of the catheter system that includes a compliant balloon integral to the distal tip.

FIG. 4 illustrates a cross-sectional view of one embodiment of the catheter system that includes a one piece fluted support structure on the distal end.

DETAILED DESCRIPTION

Figure 1:
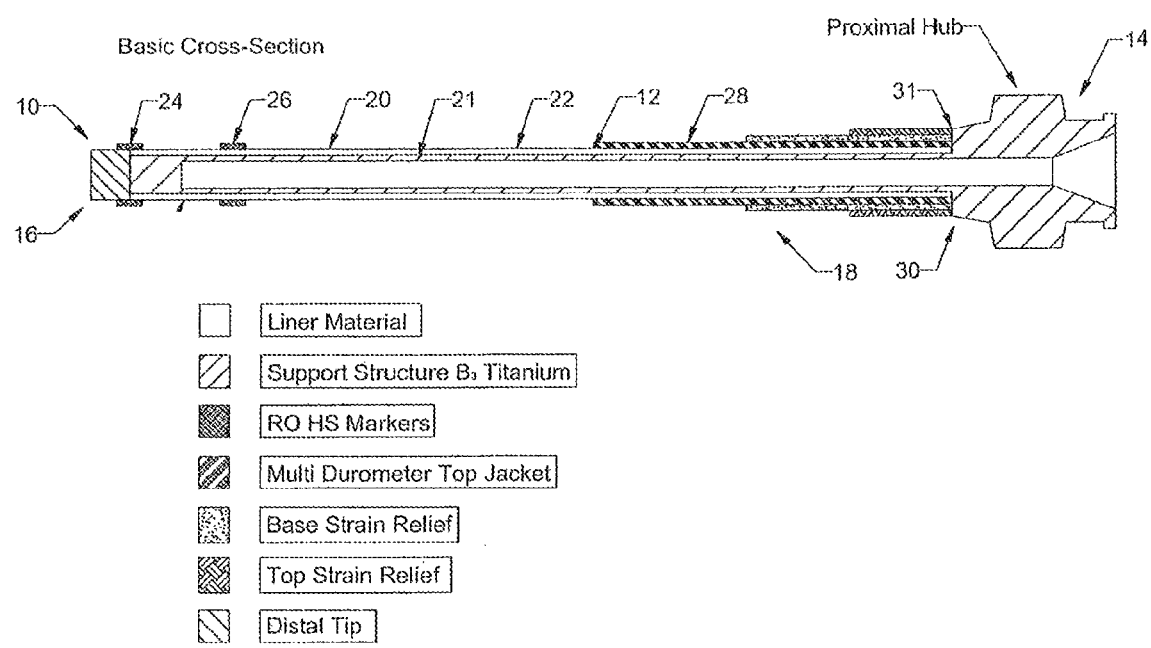
FIG. 1 illustrates a cross-sectional view of one embodiment of the catheter system of the invention.

Although detailed embodiments of the invention are disclosed herein, it is to be understood that the disclosed embodiments are merely exemplary of the invention that may be embodied in various and alternative forms. Specific structural and functional details disclosed herein are not to be interpreted as limiting, but merely as a basis for teaching one skilled in the art to variously employ the catheter embodiments. Throughout the drawings, like elements are given like numerals.

Referred to herein are trade names for materials including, but not limited to, polymers and optional components. The inventor herein does not intend to be limited by materials described and referenced by a certain trade name. Equivalent materials (e.g., those obtained from a different source under a different name or catalog (reference) number to those referenced by trade name may be substituted and utilized in the methods described and claimed herein. All percentages and ratios are calculated by weight unless otherwise indicated. All percentages are calculated based on the total composition unless otherwise indicated. All component or composition concentrations are in reference to the active level of that component or composition, and are exclusive of impurities, for example, residual solvents or by-products, which may be present in commercially available sources.

Embodiments of the invention relate to a catheter, one embodiment of which is a microcatheter, that is useful for vascular organs thereof navigation within the coronary, thoracic and peripheral vasculature of the human or other animal body. Depending on the selected diameter, catheter embodiments described herein are well suited for distal navigation and for providing a working conduit within the fine vessels of the heart, brain, hepatics, lumbar, pancreatic and other organs with fine vessels.

Embodiments of the invention include a catheter main body that defines a lumen and also includes a liner within the lumen of the catheter main body. The catheter main body also includes marker bands which are used by a physician to gauge distance at the distal end of the catheter, a coil or braid for support and torque response, a multidurometer shaft for advancement and tracking of the catheter, a hub through which navigation aids or therapies are passed into the lumen of the catheter, a strain relief attached to the distal hub and a lubricious coating over a distance of 65 cm-100 cm of the catheter. The lubricious coating that includes an opacifying material in a concentration of about 1 to 45% aids in the tracking of the catheter through the vasculature. In addition, for some embodiments, a compliant distal balloon is utilized to provide support during delivery of a device or agent as well as for partial or full occlusion of the vessel for short periods of time.

Some embodiments of the catheter system invention include a catheter main body that defines a lumen and a liner within the lumen of the catheter main body. The liner has, for some embodiments, a wall thickness of between 0.001 inches and 0.0004 inches. The liner is either extruded or dip-coated on a mandrel with an outer diameter in a range from 0.0165 inches to 0.0225 inches.

Some embodiments of the catheter system also include a support coil or braid that includes a round or flat wire that includes $\beta_3$ Titanium metal or a polymeric monofilament material from a group that includes but not limited to PEEK, Nylon, Polypropylene, Dacron polyethylene terephthalate and the like. The catheter system further includes a marker band that includes a heat shrinkable material coated with a radiopaque material is applied to a catheter body for the purpose of providing reference marks on the distal end of a catheter shaft.

The catheter system also includes a multidurometer shaft that includes materials from the Grilamid family, PEBaX, polyether block amide Urethanes, Silicones and the like that may be utilized as jacketing material for the outer catheter shaft jacket. The jacketing material is filled with an opacifying agent in a range from 1% to 50% by weight, in order to be radiopaque, with materials identified as appropriate opacifiers for fluoroscopic imaging. The opacifying agents include but are not limited to Barium Sulphate, Bismuth Bicarbonate, Tungsten and Molybdenum and the like. The jacketing material is placed at varying intervals along the length of the catheter with a stiffer material being utilized on the proximal end of the catheter and successively softer materials utilized as one moves toward the distal end of the catheter. The distal most durometer contains no radiopaque filler in order to better visualize devices being placed through the catheter lumen and into the vasculature. A hub and strain-relief are added to the proximal end of the catheter to provide a channel into which devices can be placed and gain entrance into the catheter lumen.

One embodiment of the catheter system, illustrated generally at 10 in FIG. 1 includes a catheter main body 12, having a proximal hub 14, a distal tip 16 and a shaft 18. The distal tip 16 is, for some embodiments, about one millimeter in length. The distal tip 16 is free of a support structure in order to ensure that the tip is atraumatic.

For some embodiments, the proximal portion of the shaft is more rigid than the distal portion. Markers, shown for one embodiment at 24 and 26 are placed within the distal portion of the shaft 18 wherein the markers 24 and 26 include a radiopacifying agent integrated onto a heat shrinkable material. When properly positioned, the markers 24 and 26 are drawn down onto the catheter shaft 18. For some embodiments, the distal portion of the shaft 18, proximal to the distal tip 16 includes a supporting structure 21. The markers 24 and 26 are positioned over the supporting structure 21 and provides radiopacity and also positions the support structure 21 in place.

A liner 20, having, for some embodiments, a wall thickness of between 0.001 inch and 0.0004 inch, extends the entire length of the shaft 18. For some embodiments, the catheter 10 has an outer diameter ranging from 3.8 Fr (0.051"-1.23 mm) to 1.8 Fr (0.025"-0.6 mm) and an inner diameter ranging from (0.036" 0.9 mm) to (0.010"-0.4 mm).

The liner 20 is, for some embodiments, extruded and for other embodiments, is dip-coated on a mandrel with an outer diameter within a range from 0.0165 inches to 0.0225 inches.

The catheter system embodiment 10 also includes a support coil or braid 22 that for some embodiments, includes a round or flat wire. For some embodiments, the round or flat wire includes $\beta_3$ Titanium metal. For other embodiments, the support coil or braid 22 includes a polymeric monofilament material selected from a group that includes PEEK, Nylon, Polypropylene, Dacron and other materials having similar physical and chemical properties. The support coil or braid 22 extends from a proximal end 31 of the catheter shaft to beneath a distal most marker band, shown at 24 in FIG. 1.

The $\beta_3$ Titanium braid wire displays physical properties similar to stainless steel wire and the mechanical properties of the $\beta_3$ Titanium are similar to that of Nitinol wire. These properties provide strength, resiliency and torque response to the braided or coiled catheter shaft embodiment 22 in FIG. 1. In addition, use of polymer filaments such as PEEK, Polyamide, Nylon, Polyester and other materials having similar chemical and mechanical properties as braid or coil components provide a surprisingly effective method of reinforcing a catheter shaft main body.

Further, the use of a tube made from $\beta_3$ Titanium, Nitinol or Stainless Steel or other material having similar chemical and mechanical properties into which flutes are ground, cut or etched provides a flexible frame capable of supporting the catheter shaft 18. For some embodiments, one of which is shown at 50 in FIG. 4, the flute 66 is integrated into the shaft 18 in a similar manner to a coil or braid. The flute, coil or braid provide strength, resiliency and torque response. Similarly, the extruded polymeric materials cited above such as PEEK, Polyamide, Nylon, Polyester and other similar materials, which, for some embodiments, are fluted are used to enhance catheter shaft strength, resiliency and torque response.

The catheter system embodiment 10 further includes one or more marker bands 24 and 26. The marker bands 24 and 26 include a heat shrinkable material coated with a radiopaque material. The marker bands 24 and 26 are applied to the main body 12 of the catheter for the purpose of providing reference marks for the distal end 16 of the catheter main body 12. While two marker bands, 24 and 26, are shown in FIG. 1, it is understood that catheter embodiments may include one or more marker bands. For one embodiment, the radiopaque, RO, heat shrinkable marker bands are placed one millimeter and three centimeters, respectively, from the distil tip 16 of the catheter embodiment, respectively, measured from a distil end of each marker 24 and 26.

For some embodiments, the radiopaque marker 24 or 26, includes a heat shrinkable material which is coated with a radiopaque coating and is applied to the catheter shaft 18 prior to over-jacketing the catheter with the multi durometer top jacket. The polymeric marker 24 or 26 is mechanically retained following the application of heat and subsequent shrinkage of the marker 24 or 26 to the catheter shaft 18. This method of making the catheter is advantageous over conventional manufacturing processes in that conventional precious metal markers require bonding and are costly.

The non-radiopacified distal segment of the catheter allows for better visualization of devices being placed through the catheter lumen, and improves control during placement of GDC coils, embolics, guidewires and the like.

In addition, the catheter system embodiment 10 includes a multidurometer top jacket 28 that includes one or more of materials from the Grilamid family, PEBaX, Urethanes, Silicones and other materials having similar physical and chemical properties. The multidurometer top jacket includes jacket 28, and, for the embodiment shown in FIG. 1, includes five durometers that are placed at varying intervals along the length of the catheter shaft, with a stiffer material being utilized on a proximal end of the catheter main body and successively softer materials utilized as one moves toward a distal end of the catheter main body. For some embodiments, the distal most durometer contains no radiopaque filler in order to better visualize devices being placed through the catheter lumen and into the vasculature.

Many conventional intravascular catheters designed for fine navigation within small vessels have issues not only with tracking, but also with catheter retention at the treatment site. A combination of progressively softer durometer polymer segments coupled with alternating support geometries of coils braids or a combination thereof are employed by catheter embodiments described herein to achieve improved trackability and catheter retention.

The catheter system embodiment 10 also includes a hub and strain-relief 30, which is added to the proximal end of the catheter embodiment 10 to provide a channel into which devices can be placed in order to gain entrance into the catheter lumen. The base and top strain relief's also provide protection from kinking and other delivery problems. The base strain relief is, for some embodiments, two-times the length of the top strain relief.

Embodiments of the invention address the problems described herein associated with prior art devices by employing coiling and braiding materials that display physical properties of Stainless Steel wire and mechanical properties similar to Super-elastic nitinol. Alternately, other reinforcing materials are taken from a family of polymeric filaments used to form the shaft support.—shape memory—Use of these materials results in improved tracking combined with better catheter retention at the site of treatment. The combination of materials, winding geometries and shaft over-jacket stiffness result in the desired performance characteristics. In addition, the use of a compliant distal balloon at the shaft tip ensures proper seating of the catheter during treatment.

For some embodiments, one of which is shown at 30 in FIG. 2, an echogenic coating 32 is applied to the catheter shaft and balloon 34 to allow for catheter visualization within an ultrasound imaging system.

For some embodiments, one of which is shown at 40 in FIG. 3, the catheter includes a compliant distensible distal balloon 42 integral to the catheter shaft 44. The distal balloon 42 enables a user to inflate the balloon 42 in order to anchor the catheter tip 46 at a desired location within a vessel. The distal balloon 42 may also be deployed in order to occlude flow within a vessel. The distal balloon 42 is, for some embodiments, formed by dip-coating, using materials from the families of silicone elastomers, urethane copolymers, thermoplastic elastomers and other materials having similar physical and chemical properties.

For some embodiments, the compliant balloon 42 is integral to the distal end of the catheter shaft. The balloon 42 may be inflated and deflated from a manifold hub mounted on the proximal end of the catheter. The balloon is inherently radiopaque and does not require contrast media to inflate in order to visualize under fluoroscopy. The balloon may be inflated in order to provide distal catheter tip support while delivering a therapy through the catheter as well as totally or partially occlude flow in a vessel.

The distal balloon 42 is inflated by mechanisms such as a small tubular port 48, which runs the length of the catheter shaft 44 and terminates at the distal end 46 of the catheter 40. This port 48 includes a small diameter tube that is laminated to the primary catheter shaft and overlaid with PEBaX or an appropriate jacketing material and reflowed. The proximal end of the port 48 is terminated in a proximal hub 50 that functions to inflate the distal catheter balloon. The distal end 46 of the port 48 exits within that area where the distal balloon 42 is fit to the catheter shaft 44 to provide a method for inflating the balloon 42. The distal catheter balloon 42 includes a radiopaque coating, which provides contrast when in use within a fluoroscopic field. The coating mitigates the need to use a contrast solution to fill and visualize the distal catheter balloon.

Another embodiment of the invention, illustrated at 50 in FIG. 4, includes a catheter main body 52 that defines a lumen 54 and also includes a liner 56 within the lumen 54 of the catheter main body. The catheter main body 52 may, for some embodiments, include one or more marker bands which are used by the physician to gauge distance at the distal end 56 of the catheter main body 52. The catheter system also includes a coil or braid 58 for support and torque response, a multidurometer shaft 60 for advancement and tracking of the catheter system 50, a hub 62 through which navigation aids or therapies are passed into the lumen of the catheter, a strain relief attached to the distal hub and a lubricious coating over a distance of 65 cm-100 cm of the lumen. The lubricious coating aids in the tracking of the catheter system through the vasculature. In addition, for some embodiments, a compliant distal balloon 64 is utilized to provide support during delivery of a device or agent as well as for partial or full occlusion of the vessel for short periods of time.

For some embodiments, the coil pitch is altered or alterable at mid-shaft or at a distal end of the catheter to facilitate variable degrees of stiffness based on the number of the pitch. Alteration of pitch also facilitates catheter tip forming and shape retention in use. For system embodiments where braid is used, PICS per inch are altered or alterable at mid-shaft or at a distal end of the catheter to facilitate variable degrees of stiffness based on the number of the PICS.

One embodiment of the catheter system also includes a one piece fluted support structure 66 on or proximal to the distal catheter end 56.

In accordance with embodiments of the invention, the catheter system 10 is intended for introduction and navigation within the fine vessels of the heart, brain, spine, liver, hepatics, lumbar, pancreatic and other organs with fine vessels.

Embodiments of the invention include making the catheter system by making or obtaining a luminous hollow tube wherein the hollow liner is covered with a supporting structure in the form of a braid or coil made by using materials from the Titanium family or polymer filaments such as PEEK, Polyamide, Nylon, Polyester or other materials having similar physical and chemical properties over which polymeric materials of varying durometers are place proximal to distal. The proximal portion of the shaft is more rigid than the distal segment.

Markers are placed at the distal end of the shaft. The markers include a radiopacifying agent integrated onto a heat shrinkable material. When properly positioned, the markers are drawn down onto the catheter shaft over the supporting structure, providing radiopacity and holding the support structure in place.

For some embodiments, an outer jacket of varying material durometers is applied over the liner/supporting structure and the jacketing segments are reflowed over the shaft resulting in a uniform transition of stiffer (proximally) to more compliant material (distally) at the end of the catheter shaft.

For some embodiments, a lubricious layer is bound to the outer surface of the catheter shaft for a distance of 65 Cm to 100 Cm for the purpose of making tracking of the catheter within a guiding catheter or vessel smoother and less traumatic.

The proximal end of the shaft has a hub and strain relief mounted onto the shaft by mechanisms that include but not limited to bonding and insert molding. The strain relief provides additional support to the hub and shaft transition.

Yet another embodiment of the invention includes the incorporation of an echogenic coating onto the catheter shaft which will enable device visualization within an ultrasound imaging system.

Figure 5:
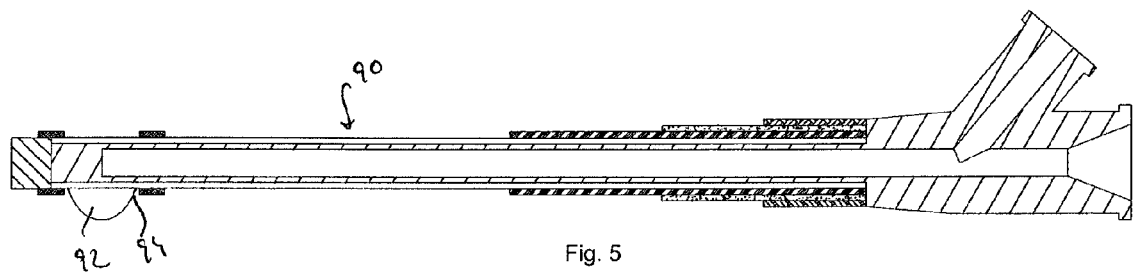
FIG. 5 illustrates a cross-sectional view of a catheter system that includes a balloon effective for selective inflation.

One more embodiment, illustrated at 90 in FIG. 5, illustrates a system embodiment, previously described herein, having a balloon 92, expandable in only one direction. The balloon 92 is mounted to a catheter shaft 94. The direction of expansion depends upon how the balloon is formed and mounted to the catheter shaft 94.

Since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes, which come within the meaning and range of equivalency of the claims, are intended to be embraced therein.

What is claimed is:

1. A vascular microcatheter, comprising:
   a lumen having a distal end and a proximal end and a liner within the lumen;
   one or more marker bands circumferentially arranged around the lumen;
   a support structure extending from the proximal end of the lumen to the most distal marker band; a top jacket positioned annularly with respect to the lumen, comprising five durometers of material wherein softer materials are positioned distally, wherein the support structure and top jacket alternate along the length of the vascular microcatheter, and further comprising a lubricious coating that includes an opacifying material in a concentration of about 1 to 45% effective for tracking the vascular microcatheter through vasculature and an echogenic coating on the distal end of the lumen, the vascular microcatheter further comprising a distensible distal balloon wherein the distensible distal balloon comprises a radiopaque coating and a distal echogenic coating.

2. The vascular microcatheter of claim 1, wherein the support structure comprises a support coil or braid.

3. The vascular microcatheter of claim 1, wherein the support structure comprise one or more of beta (3) titanium, PEEK, nylon, polypropylene, and polyethylene terephthalate.

4. The vascular microcatheter of claim 1, further comprising a distal tip that is free of the support structure.

5. The vascular microcatheter of claim 1, wherein the top jacket comprises one or more of a homopolyamide nylon, polyether block amide, urethanes, and silicones.

6. The vascular microcatheter of claim 1 wherein the top jacket five durometers are placed at varying intervals along the length of the vascular microcatheter.

7. The vascular microcatheter of claim 1, further comprising a hub and strain relief positioned at the proximal end of the vascular microcatheter lumen.

8. The vascular microcatheter of claim 1, further comprising a one piece fluted support structure positioned on the distal end of the vascular microcatheter.

\* \* \* \* \*

UNITED STATES PATENT AND TRADEMARK OFFICE
CERTIFICATE OF CORRECTION

| | | |
|---|---|---|
| PATENT NO. | : 8,911,400 B2 | Page 1 of 1 |
| APPLICATION NO. | : 12/028394 | |
| DATED | : December 16, 2014 | |
| INVENTOR(S) | : Steven J. Ferry | |

It is certified that error appears in the above-identified patent and that said Letters Patent is hereby corrected as shown below:

On Title page 2, in column 2, item (56) under "Other Publications", line 4, delete "rnailed" and insert --mailed--, therefor In the Claims In column 8, line 11, in Claim 1, after "band;", insert --¶--, therefor Signed and Sealed this
Twenty-ninth Day of September, 2015

Michelle K. Lee
*Director of the United States Patent and Trademark Office*